(12) United States Patent
Miyazaki

(10) Patent No.: US 12,020,447 B2
(45) Date of Patent: Jun. 25, 2024

(54) IMAGE PROCESSING TO OBTAIN A STILL IMAGE WITH A HIGH IMAGE QUALITY BY COMBINING MULTIPLE FRAME IMAGES OF A DYNAMIC IMAGE

(71) Applicant: Konica Minolta, Inc., Tokyo (JP)

(72) Inventor: Haruhiko Miyazaki, Toyohashi (JP)

(73) Assignee: KONICA MINOLTA, INC., Tokyo (JP)

( * ) Notice: Subject to any disclaimer, the term of this patent is extended or adjusted under 35 U.S.C. 154(b) by 208 days.

(21) Appl. No.: 17/330,983

(22) Filed: May 26, 2021

(65) Prior Publication Data

US 2021/0383558 A1    Dec. 9, 2021

(30) Foreign Application Priority Data

Jun. 3, 2020  (JP) ................... 2020-096535

(51) Int. Cl.
*G06T 7/33*    (2017.01)
*G06T 5/50*    (2006.01)
*G06T 7/00*    (2017.01)
*G06T 7/73*    (2017.01)

(52) U.S. Cl.
CPC ............ *G06T 7/337* (2017.01); *G06T 5/50* (2013.01); *G06T 7/0012* (2013.01); *G06T 7/74* (2017.01); *G06T 2207/20212* (2013.01)

(58) Field of Classification Search
CPC . G06T 2207/10016; G06T 2207/10116; G06T 2207/30061; G06T 7/32
See application file for complete search history.

(56) References Cited

U.S. PATENT DOCUMENTS 8,569,706 B2 * 10/2013 Thiruvenkadam ... A61B 6/5288
                                                  250/363.03
2021/0383558 A1 * 12/2021 Miyazaki .................. G06T 7/74

FOREIGN PATENT DOCUMENTS

JP    2010-119852 A    6/2010
JP    2012-003503 A    1/2012
JP    2018-129738 A    8/2018

OTHER PUBLICATIONS

Japan Patent Office, "Notice of Reasons for Refusal" mailed Nov. 28, 2023 for related Japanese patent application No. 2020-096535 and its English translation, 6 pages.

* cited by examiner

*Primary Examiner* — Gandhi Thirugnanam
(74) *Attorney, Agent, or Firm* — Lucas & Mercanti, LLP

(57) ABSTRACT

A non-transitory recording medium storing a computer readable program that causes a computer to perform position aligning, accuracy calculating, and image combining. The position aligning is performing position alignment of other frame images with respect to one reference frame image selected from among multiple frame images that form a dynamic image. The accuracy calculating is calculating an accuracy of the position alignment for each pixel of each of the other frame images. The image combining is combining the reference frame image with the other frame images after the position alignment to generate one composite still image. In the image combining, the computer performs weighting and generates the one composite still image, the weighting being processing of changing a composition ratio between the other frame images for each pixel according to the accuracy calculated by the accuracy calculating.

7 Claims, 6 Drawing Sheets

FIG.5A w,wa
FIG.5B w,wb
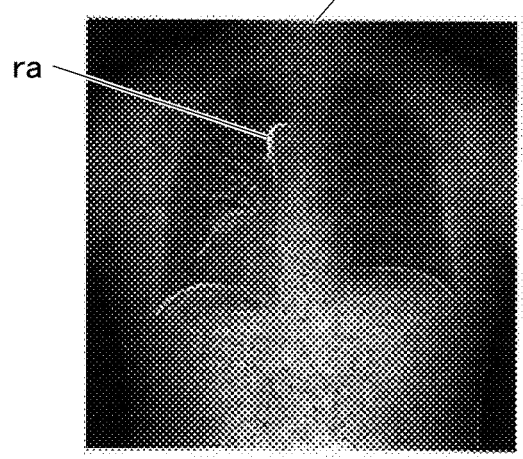
FIG.5C w,wc
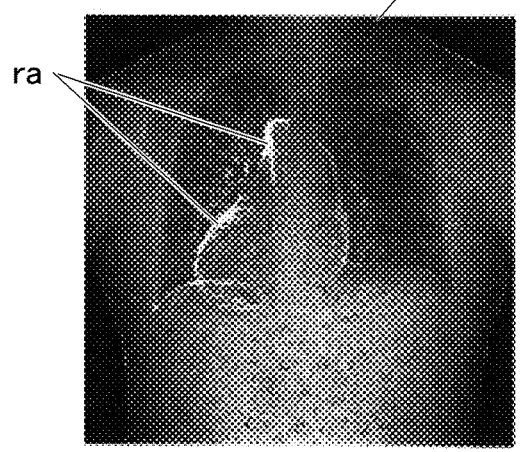
FIG.5D w,wd
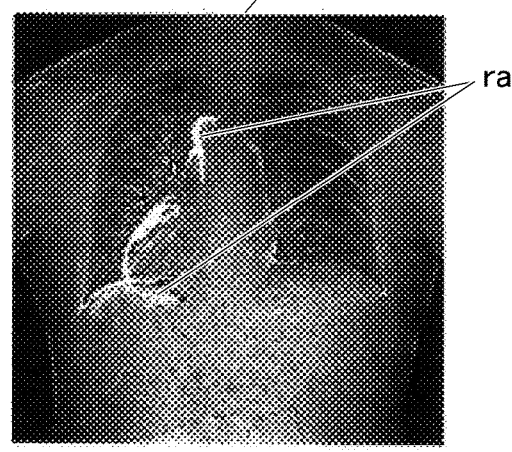
FIG.5E w,we
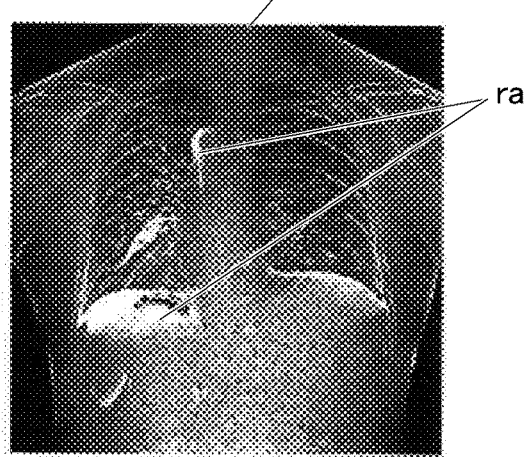
FIG.5F w,wf
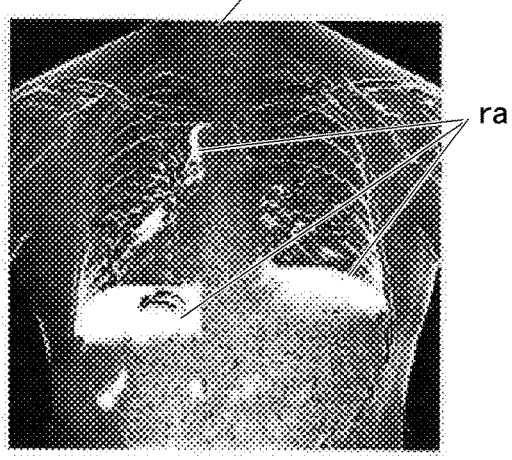

IMAGE PROCESSING TO OBTAIN A STILL IMAGE WITH A HIGH IMAGE QUALITY BY COMBINING MULTIPLE FRAME IMAGES OF A DYNAMIC IMAGE

CROSS-REFERENCE TO RELATED APPLICATIONS

The entire disclosure of Japanese Patent Application No. 2020-096535 filed on Jun. 3, 2020 is incorporated herein by reference in its entirety.

BACKGROUND

Technological Field

The present invention relates to a recording medium, an image processing apparatus, and an image processing method.

Description of the Related Art

In recent years, radiation imaging has enabled obtaining an image (which is called a dynamic image) capturing the movement of a target site (site which is a target of test and diagnosis) in a living body by performing continuous imaging for a short time. Such a dynamic image enables checking the movements of lungs and diaphragm during breathing and the movements such as dilatation and contraction of the heart.

However, diagnosis may also require checking the target site of the diagnosis not only with the image having a movement but also with a still image.

In a case where the moving image is configured by including multiple images which were obtained by continuous imaging as in the dynamic image, imaging is performed by emitting radiation of a relatively low dose in order to suppress the exposure level.

Thus, taking one of the images only obtains an image which has a very low image quality compared to a still image which is obtained by general imaging.

On the other hand, when general imaging to obtain the still image is also performed separately from imaging of the dynamic image, the exposure level is increased for the amount of the general imaging, which is not preferable.

On this respect, for example, JP 2012-003503 A discloses a technique for generating a single corrected image from among multiple images.

The technique described in JP 2012-003503 A aims to generate a composite still image with a high image quality by sequentially combining images other than a reference frame image with the reference frame image ("reference image" in JP 2012-003503 A).

When it is possible to obtain a single still image by combining multiple images, it is not necessary to perform both of imaging of a dynamic image and general imaging, and thus, it is possible to obtain the dynamic image and the still image without increasing the exposure level.

The technique described in JP 2012-003503 A derives an image movement amount from the reference frame image for each of multiple regions included in the image, sets a weighting value for each of multiple partial regions such that an image having a larger image movement amount has a smaller weighting value, and sequentially combines the other images with the reference frame image according to the weighting value which was set for each image.

That is, the technique calculates the image movement amount (relative movement amount) between frames for each image partial region, performs position alignment processing to use a small weighting value for image composition when the image movement amount is large and to use a large weighting value for image composition when the image movement amount is small, and combines images according to the weighting values.

SUMMARY

However, whether or not it is possible to obtain a composite still image with a high image quality from multiple images depends on the accuracy of position alignment rather than the image movement amount.

The accuracy of position alignment can be high even when the image movement amount is large, and in reverse, the accuracy of position alignment can be low even when the image movement amount is small, depending on the site.

Thus, there is a problem that, when the weighting at the time of image combining is determined on the basis of image movement amount, the weighting is not performed appropriately from the viewpoint of the image quality of the composite still image, and it may not be possible to obtain a composite still image with a high image quality and a high resolution.

An object of the present invention is to provide a recording medium, an image processing apparatus, and an image processing method that can obtain a still image with a high image quality by combining multiple frame images that form a dynamic image.

To achieve at least one of the abovementioned objects, according to an aspect of the present invention, a recording medium reflecting one aspect of the present invention is a non-transitory recording medium storing a computer readable program that causes a computer to perform: position aligning that is performing position alignment of other frame images with respect to one reference frame image, the one reference frame image being a reference frame image selected from among multiple frame images that form a dynamic image, and the other frame images being other than the reference frame image; accuracy calculating that is calculating an accuracy of the position alignment for each pixel of each of the other frame images; and image combining that is combining the reference frame image with the other frame images after the position alignment to generate one composite still image, wherein in the image combining, the computer performs weighting and generates the one composite still image, the weighting being processing of changing a composition ratio between the other frame images for each pixel according to the accuracy calculated by the accuracy calculating.

To achieve at least one of the abovementioned objects, according to another aspect of the present invention, an image processing apparatus reflecting one aspect of the present invention comprises a hardware processor that: performs position alignment of other frame images with respect to one reference frame image, the one reference frame image being a reference frame image selected from among multiple frame images that form a dynamic image, and the other frame images being other than the reference frame image; calculates an accuracy of the position alignment for each pixel of each of the other frame images; and combines the reference frame image with the other frame images after the position alignment to generate one composite still image, wherein the hardware processor performs weighting and generates the one composite still image, the weighting being processing of changing a composition ratio between the other frame images for each pixel according to the calculated accuracy.

To achieve at least one of the abovementioned objects, according to another aspect of the present invention, an image processing method reflecting one aspect of the present invention comprises position aligning that is performing position alignment of other frame images with respect to one reference frame image, the one reference frame image being a reference frame image selected from among multiple frame images that form a dynamic image, and the other frame images being other than the reference frame image; accuracy calculating that is calculating an accuracy of the position alignment for each pixel of each of the other frame images; and image combining that is combining the reference frame image with the other frame images after the position alignment to generate one composite still image, wherein in the image combining, weighting is performed and the one composite still image is generated, the weighting being processing of changing a composition ratio between the other frame images for each pixel according to the accuracy calculated by the accuracy calculating.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein:

FIG. 5A is a view showing an example of an accuracy of position alignment, and shows an example of the best accuracy of position alignment;

FIG. 5B is a view showing an example of an accuracy of position alignment;

FIG. 5C is a view showing an example of an accuracy of position alignment;

FIG. 5D is a view showing an example of an accuracy of position alignment;

FIG. 5E is a view showing an example of an accuracy of position alignment;

FIG. 5F is a view showing an example of an accuracy of position alignment, and shows an example of the worst accuracy of position alignment;

DETAILED DESCRIPTION OF EMBODIMENTS

Hereinafter, one or more embodiments of a recording medium, an image processing apparatus and an image processing method according to the present invention will be described with reference to FIGS. 1 to 6C.

The following embodiment is provided with various technically preferable limitations for carrying out the present invention. However, the scope of the invention is not limited to the disclosed embodiments or the illustrated examples.

The image processing apparatus in the present embodiment is provided in a medical image system, and especially performs analysis and image processing of a dynamic image D (see FIG. 3) among images (medical images) obtained with various types of modalities.

Figure 1:
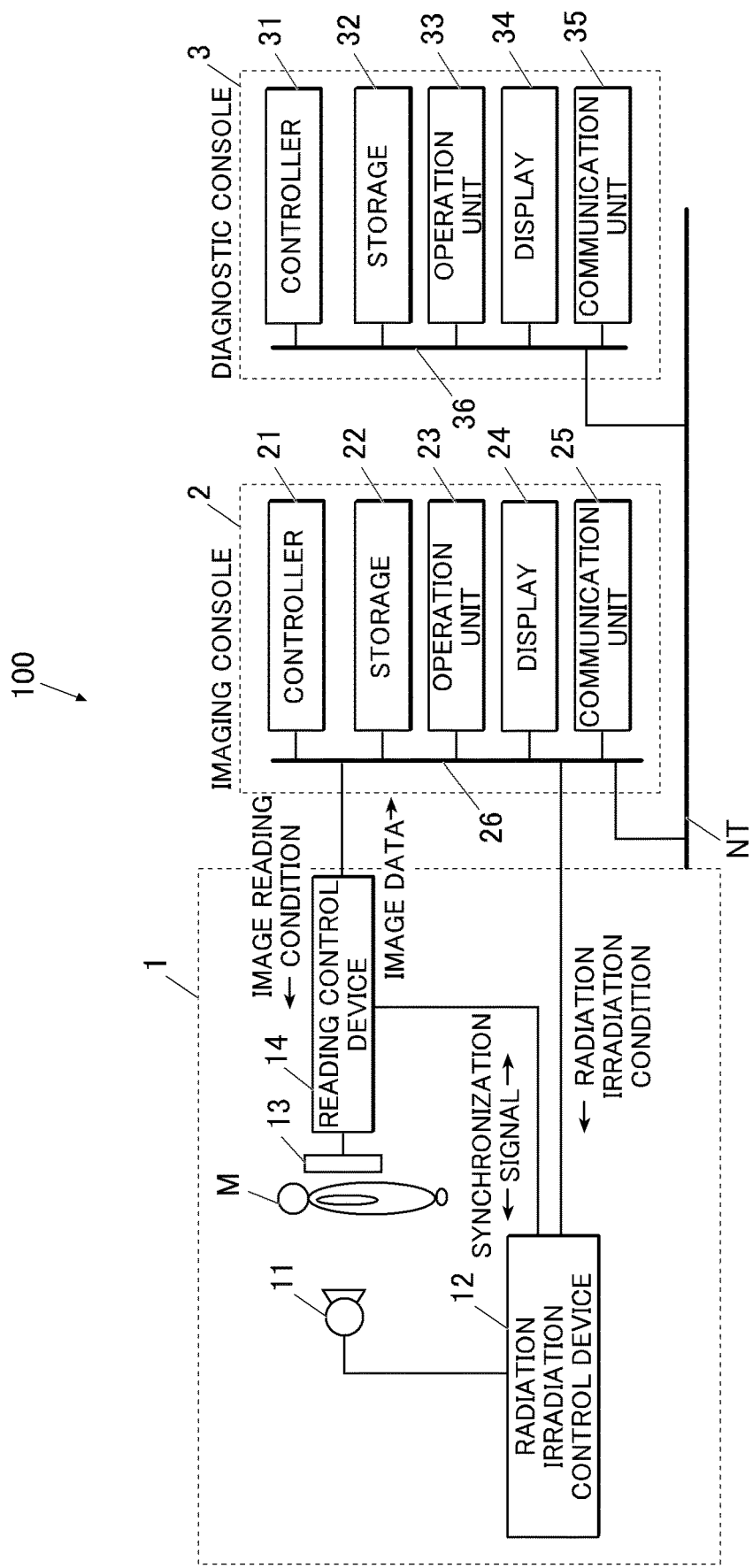
FIG. 1 is a main part configuration diagram showing a system configuration of a medical image system including an image processing apparatus in an embodiment.

FIG. 1 is a view showing the entire configuration of a medical image system 100 in the present embodiment.

As shown in FIG. 1, the medical image system 100 is configured by connecting an imaging apparatus 1 and an imaging console 2 via a communication cable or the like, and connecting the imaging console 2 and a diagnostic console 3 via a communication network NT such as a LAN (Local Area Network). The apparatuses forming the medical image system 100 are based on the DICOM (Digital Image and Communications in Medicine) standard, and the communication between the apparatuses are performed according to the DICOM standard.

As mentioned later, in the present embodiment, the diagnostic console 3 functions as the image processing apparatus.

(Configuration of Imaging Apparatus 1)

The imaging apparatus 1 is an imaging unit that performs imaging of a dynamic state of a living body such as a state change between inflation and deflation in lungs caused by the respiratory movement, a heartbeat, and the like, for example.

As shown in FIG. 1, the imaging apparatus 1 includes a radiation source 11, a radiation irradiation control device 12, a radiation detector 13, and a reading control device 14.

The dynamic imaging is obtaining images by performing radiographic imaging of a subject including a target site in a living body (for example, a portion around a lung field of a chest, a heart, or the like). The dynamic imaging is obtaining multiple images by repeatedly emitting pulsed radiation such as an X-ray at predetermined tune intervals to a subject (pulse emission) or continuously emitting radiation at a low does rate without interruption (continuous emission) to the subject. A series of images obtained by the dynamic imaging is called a dynamic image D. The data for one imaging of the dynamic image D is formed of multiple images, and the images forming the dynamic image D are referred to as frame images (frame images d1 to dn in FIG. 3).

The following embodiment is described by taking, as an example, a case where the dynamic imaging is performed by pulse emission. Though the following embodiment is described by taking, as an example, a case where the target site which is the target of diagnosis is a portion around the lung field of the chest (lung field or diaphragm), the target site is not limited to this. The target site may be a heart, pulmonary blood vessel, intercostal muscle, and thorax for a case of a chest, bowel and esophagus for a case of a stomach, and other various shape forming sites, various types of structures and the like, such as a knee, elbow, neck and spine, for example.

The radiation source 11 is arranged at a position facing the radiation detector 13 via the subject M and emits radiation (X-ray) to the subject M in accordance with control of the radiation irradiation control device 12.

The radiation irradiation control device 12 is connected to the imaging console 2, and controls the radiation source 11 to perform radiographic imaging on the basis of radiation irradiation conditions which were input from the imaging console 2. The radiation irradiation conditions input from the imaging console 2 include, for example, a pulse rate, a pulse width, a pulse interval, the number of imaging frames per imaging, a value of X-ray tube current, a value of X-ray tube voltage, the type of additional filter, and the like. The pulse rate is the number of radiation irradiations per second, and matches an after-mentioned frame rate. The pulse width is a radiation irradiation time per radiation irradiation. The pulse interval is a time from start of one radiation irradiation to start of next radiation irradiation, and matches an after-mentioned frame interval.

The radiation detector 13 is configured by including a semiconductor image sensor such as an FPD. The FPD includes a glass substrate, for example, and multiple detection elements (pixels) that are arranged in a matrix at predetermined positions on the substrate surface, and the detection elements (pixels) detect radiation which was emitted from the radiation source 11 and transmitted through at least the subject M according to its intensity, and converts the detected radiation into electric signals and accumulate the electric signals. Each pixel is configured by including a switching section such as a TFT (Thin Film Transistor). As the FPD, there are an indirect conversion type that converts the X-ray into electric signals with photoelectric conversion elements via a scintillator, and a direct conversion type that converts X-ray into electric signals directly. Either type of FPD may be used. In the present embodiment, the pixel value (density value) of image data generated in the radiation detector 13 is higher as the transmitting amount of radiation is larger.

The radiation detector 13 is provided to face the radiation source 11 via the subject M.

The reading control device 14 is connected to the imaging console 2. The reading control device 14 controls the switching sections of respective pixels of the radiation detector 13 on the basis of the image reading conditions input from the imaging console 2, to switch the reading of electric signals accumulated in the respective pixels, and obtains the image data by reading the electric signals accumulated in the radiation detector 13. The image data is frame images d1 to dn. The reading control device 14 outputs the obtained frame images to the imaging console 2. The image reading conditions include a frame rate, a frame interval, a pixel size, and an image size (matrix size), for example. The frame rate is the number of frame images obtained per second, and matches the pulse rate. The frame interval is the time from start of one operation obtaining a frame image to the start of next operation obtaining a frame image, and matches the pulse interval.

The radiation irradiation control device 12 and the reading control device 14 are connected to each other, and synchronize the radiation irradiation operation with the image reading operation by transmitting and receiving synchronization signals to and from each other.

[Configuration of Imaging Console 2]

The imaging console 2 outputs the radiation irradiation conditions and the image reading conditions to the imaging apparatus 1 to control radiation imaging and reading operation of radiographic images which are performed by the imaging apparatus 1, and displays the dynamic image obtained by the imaging apparatus 1 for an imaging operator such as an imaging technologist to confirm positioning and check whether the dynamic image is appropriate for diagnosis.

As shown in FIG. 1, the imaging console 2 includes a controller 21, a storage 22, an operation unit 23, a display 24, and a communication unit 25. The units are connected via a bus 26.

The controller 21 is configured by including a CPU (Central Processing Unit), a RAM (Random Access Memory) and the like. In response to the operation to the operation unit 23, the CPU of the controller 21 reads out system programs and various types of processing programs stored in the storage 22 to load them into the RAM, executes various types of processing including after-mentioned imaging control processing in accordance with the loaded programs, and performs centralized control of the operations of the units in the imaging console 2 and the radiation irradiation operation and the reading operation of the imaging apparatus 1.

The storage 22 is configured by including a nonvolatile semiconductor memory a hard disk or the like. The storage 22 stores data of various programs to be executed by the controller 2, parameters necessary for performing the processing by the programs, processing results and the like. For example, the storage 22 stores a program for executing imaging control processing shown in FIG. 2. The storage 22 also stores the radiation irradiation conditions and the image reading conditions so as to be associated with the imaging site. The various types of programs are stored in the form of a readable program code, and the controller 21 sequentially executes the operation according to the program code.

The operation unit 23 is configured by including a keyboard including cursor keys, numeric input keys and various types of function keys, and a pointing device such as a mouse. The operation unit 23 outputs an instruction signal which was input by a key operation made to the keyboard or a mouse operation to the controller 21. The operation unit 23 may include a touch panel on the display screen of the display 24, and in this case, the operation unit 23 outputs the instruction signal input via the touch panel to the controller 21.

The display 24 is configured by including a monitor such as an LCD (Liquid Crystal Display) and a CRT (Cathode Ray Tube), and displays an input instruction, data and the like from the operation unit 23 in accordance with the instruction of display signal input from the controller 21.

The communication unit 25 includes a LAN adapter, modem, TA (Terminal Adapter)) and the like. The communication unit 25 controls transmitting and receiving of data to and from other apparatuses which are connected to the communication network NT.

[Configuration of Diagnostic Console 3]

The diagnostic console 3 is an image processing apparatus that obtains a dynamic image D from the imaging console 2, performs image processing to the obtained dynamic image D, generates images and various types of data as processing results, and displays the generated processing results to provide information for supporting diagnosis by doctors.

As shown in FIG. 1, the diagnostic console 3 is configured by including a controller 31 (hardware processor), a storage 32, an operation unit 33, a display 34, and a communication unit 35. The units are connected via a bus 36.

The controller 31 is configured by including a CPU, a RAM and the like. In response to the operation to the operation unit 33, the CPU of the controller 31 reads out system programs and various types of processing programs stored in the storage 32 to load them into the RAM, executes various types of processing including after-mentioned image processing in accordance with the loaded programs, and performs centralized control of the operations of the units in the diagnostic console 3.

As mentioned later, the controller 31 in the present embodiment functions as a position alignment processing unit that performs, with respect to one reference frame image dh selected from among multiple frame images d1 to dn forming the dynamic image D, position alignment of the other frame images db.

The controller 31 also functions as an accuracy calculation unit that calculates the accuracy of position alignment for each of pixels of each of the other frame images df after the position alignment.

The controller 31 also functions as an image combination unit that combines the reference frame image dh with the other frame images df after the position alignment to generate one composite still image ds. In the present embodiment, the controller 31 as the image combination unit performs weighting of changing the composition ratios between the other frame images df for each pixel according to the accuracy that the controller 31 calculated as the accuracy calculation unit.

The controller 31 also functions as a determination unit that determines whether or not it is possible to generate the composite still image ds from the multiple frame images d1 to dn on the basis of the accuracy that the controller 31 calculated as the accuracy calculation unit.

The controller 31 as the determination unit determines that it is not possible to generate the composite still image ds when it is determined that the quality of the composite still image ds obtained by combining the frame images d1 to dn will be equal to or less than a predetermined standard.

The controller 31 also functions as a display control unit that controls displaying of the display 34. The controller 31 as the display control unit causes the display 34 to display the composite still image ds when the composite still image ds is generated.

In the present embodiment, the controller 31 as the display control unit may perform control to display a numerical value indicating a quality of the composite still image ds (hereinafter, referred to as a "quality value") in addition to displaying of the composite still image ds. Thus, the user can objectively judge the quality of composite still image ds.

The above respective functions of the controller 31 will be described in detail later.

The storage 32 is configured by including a nonvolatile semiconductor memory, a hard disk or the like. The storage 32 stores data of various types of programs including a program for the controller 31 to perform image analysis processing and the like, parameters necessary for performing the processing by the programs, processing results and the like. The various types of programs are stored in the form of a readable program code, and the controller 31 sequentially executes the operation according to the program code.

The storage 32 stores the dynamic image D which was obtained in the past and various types of data obtained by performing various types of image processing to the dynamic image D. The location to store the dynamic image D and to store various types of data obtained by performing image processing to the dynamic image D is not limited to the storage 32 in the diagnostic console 3. For example, the dynamic image D and the various types of data may be stored in a storage, a server or the like provided outside the diagnostic console 3.

The operation unit 33 is configured by including a keyboard including cursor keys, numeric input keys and various types of function keys, and a pointing device such as a mouse. The operation unit 33 outputs an instruction signal which was input by a key operation made to the keyboard or a mouse operation to the controller 31. The operation unit 33 may include a touch panel on the display screen of the display 34, and in this case, the operation unit 33 outputs the instruction signal input via the touch panel to the controller 31.

The display 34 is configured by including a monitor such as an LCD and a CRT, and performs various types of displaying in accordance with the display signal input from the controller 31.

The display 34 in the present embodiment is able to display the composite still image ds and the quality value of the composite still image ds.

When the controller 31 as the determination unit determines that it is not possible to generate the composite still image ds, the display 34 in the present embodiment notifies the user that it is not possible to generate the composite still image ds, that is, the display 34 functions as a notifier. In this case, the display 34 displays an error message such as "The composite still image cannot be created from this dynamic image.", for example.

The specific displaying on the display 34 will be described in detail later.

The communication unit 35 includes a LAN adapter, modem, TA and the like. The communication unit 35 controls transmitting and receiving of data to and from other apparatuses which are connected to the communication network NT.

[Operation of Diagnostic Console as Image Processing Apparatus]

Next, the operation of diagnostic console 3 as the image processing apparatus will be described.

The imaging operation by the imaging apparatus 1 and the imaging console 2 for obtaining the dynamic image will be described first.

To perform imaging, the imaging operator operates the operation unit 23 of the imaging console 2, to input patient information (name, height, weight, age, sex and the like of the patient) of the object (subject M), test information and the like.

The test information is, for example, the target site which is a target of imaging (for example, lung field, diaphragm, or the like), the type/manner of movement of the target site or tissue change (whether the movement is dilatation-contraction movement or up-down movement, for example), positioning during imaging (front, lateral, or the like), and imaging conditions of the imaging (tube voltage, irradiation angle, imaging time, and the like).

The radiation irradiation conditions are read out from the storage 22 to be set in the radiation irradiation control device 12, the image reading conditions are read out from the storage 22 to be set in the reading control device 14, and the instruction of radiation irradiation buy the operation made to the operation unit 23 is waited.

The imaging operator locates the subject M between the radiation source 11 and the radiation detector 13 to perform positioning.

In a case where the dilatation-contraction movement of the lung field or up-down movement of the diaphragm is captured as the dynamic image D, for example, in order to perform imaging under the breathing state, the object (subject M) is instructed to be at ease and prompted to perform quiet breathing. At the time when the preparation for imaging is completed, the imaging operator operates the operation unit 23 to input the radiation irradiation instruction. In the imaging, guidance of the timing to breathe in, the timing to stop breathing and the timing to breathe out may be performed by automatic voice guidance.

When the radiation irradiation instruction is input via the operation unit 23, the imaging start instruction is output to the radiation irradiation control device 12 and the reading control device 14, and dynamic imaging is started. That is, radiation is emitted by the radiation source 11 at the pulse interval set in the radiation irradiation control device 12, and frame images d1 to dn are obtained by the radiation detector 13.

Next, the image processing method of generating the composite still image ds from the dynamic image D in the present embodiment will be described with reference to FIGS. 2 and 3.

Figure 2:
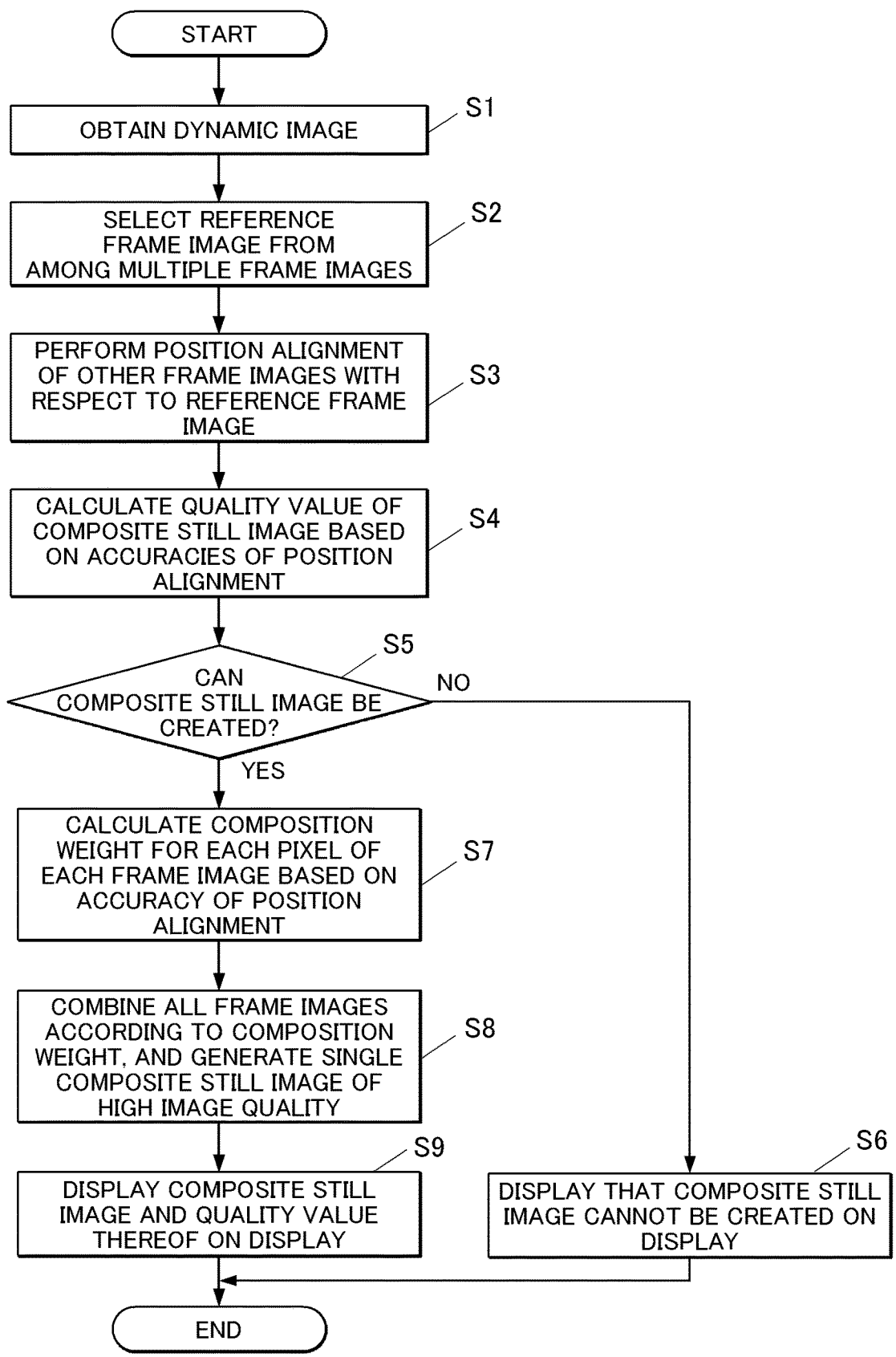
FIG. 2 is a flowchart showing the procedure of image processing in the embodiment.
Figure 3:
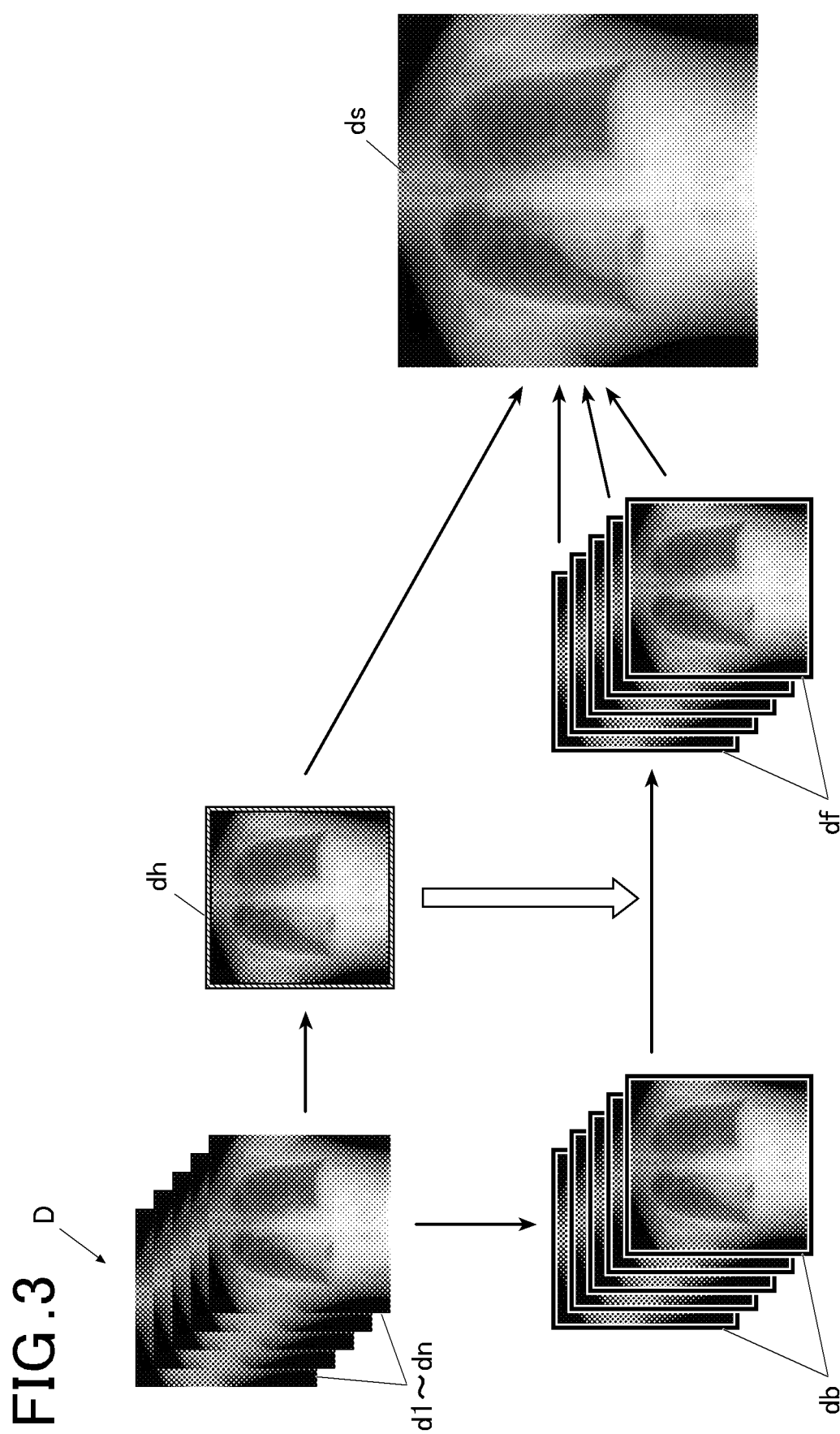
FIG. 3 is an explanation view schematically showing the procedure of image processing in the embodiment.

FIG. 2 is a flowchart showing the image processing method, and FIG. 3 is an explanation view schematically showing the flow of main processes to generate the composite still image ds from the dynamic image D.

When imaging of dynamic image D is performed by the imaging apparatus 1, the frame images d1 to dn forming the dynamic image D are sequentially input to the imaging console 2, and associated with the numbers indicating the respective imaging orders (frame numbers).

The series of frame images d1 to dn of the dynamic image D are received by the diagnostic console 3 from the imaging console 2 via the communication unit 35. Thus, the dynamic image D (first dynamic image) is obtained by the diagnostic console 3 (step S1), and the image processing shown in FIG. 2 is executed by the cooperation between the controller 31 and the program stored in the storage 32.

To be specific, one reference frame image dh is selected from among the multiple frame images d1 to dn forming the obtained dynamic image D (step S2).

The method to select the reference frame image dh is not particularly limited. The user may arbitrarily select one reference frame image dh, or the controller 31 of the diagnostic console that is the image processing apparatus may automatically select one reference frame image dh.

The method of automatic selection by the controller 31 is, for example, the following method.

That is, for example, a model image is stored in ti storage 32 or the like, and a frame image which has the smallest difference from the model image among the frame images d1 to dn is selected as the reference frame image dh.

The model image is a still image which is a model of a composite still image ds. For example, in a case where a composite still image ds used in still image diagnosis is to be generated, an image of a subject in a predetermined state (for example, maximum inspiratory level or maximum expiratory level in a case of a chest) can be used as a model image. In a case where a composite still image ds used in comparative radiographic image interpretation is to be generated, a still image which captured a same site of a same patient in the past (or a composite still image generated from a dynamic image which captured a same site of a same patient in the past) may be used as a model image, for example.

Though not particularly limited, the difference between the model image and each of the frame images d1 to dh may be obtained by the following method. For example, each of the frame images d1 to dn forming tie obtained dynamic mage D may be analyzed to calculate the square error with respect to the model image, and the frame image which has the smallest square error among the square errors calculated from the frame images d1 to dn may be automatically determined as the reference frame image dh. Each of the frame images d1 to dn forming the obtained dynamic mage D may be analyzed to calculate a correlation coefficient with respect to the model image, and the frame image which has the largest correlation coefficient among the correlation coefficients calculated from the frame images d1 to dn may be automatically determined as the reference frame image dh.

When the reference frame image dh is determined, the controller 31 as the position alignment processing unit performs position alignment (registration) of the other frame images db with respect to the reference frame image dh (step S3).

The position alignment (registration) of the other frame images db with respect to the reference frame image dh indicates preparing two images that are the reference frame image dh and one image to perform position alignment (one of the other frame images db) and performing deformation processing such as parallel movement, rotation and expansion/contraction to the frame image db such that the frame image db to perform position alignment approaches the reference frame image dh.

After position alignment (registration) of the other frame images db (frame images on the left side of the white arrow directed downward from the reference frame image dh in FIG. 3 are referred to as frame images db before position alignment), the controller 31 calculates the accuracy of position alignment for each of the frame images df after the positon alignment (frame images on the right side of the white downward arrow from the reference frame image dh in FIG. 3 are referred to as frame images df after position alignment).

In the present embodiment, the accuracy of position alignment is calculated by obtaining the difference between the reference frame image dh and each of the frame images df after the position alignment for each of the pixels. The method for calculating the accuracy of position alignment is not limited to this. For example, as another calculation method, the accuracy of position alignment may be calculated by a cross-correlation coefficient or the like.

Whether or not a composite still image ds of a high image quality can be obtained by combining the multiple frame images d1 to dn depends on the accuracy of position alignment.

Figure 4A:
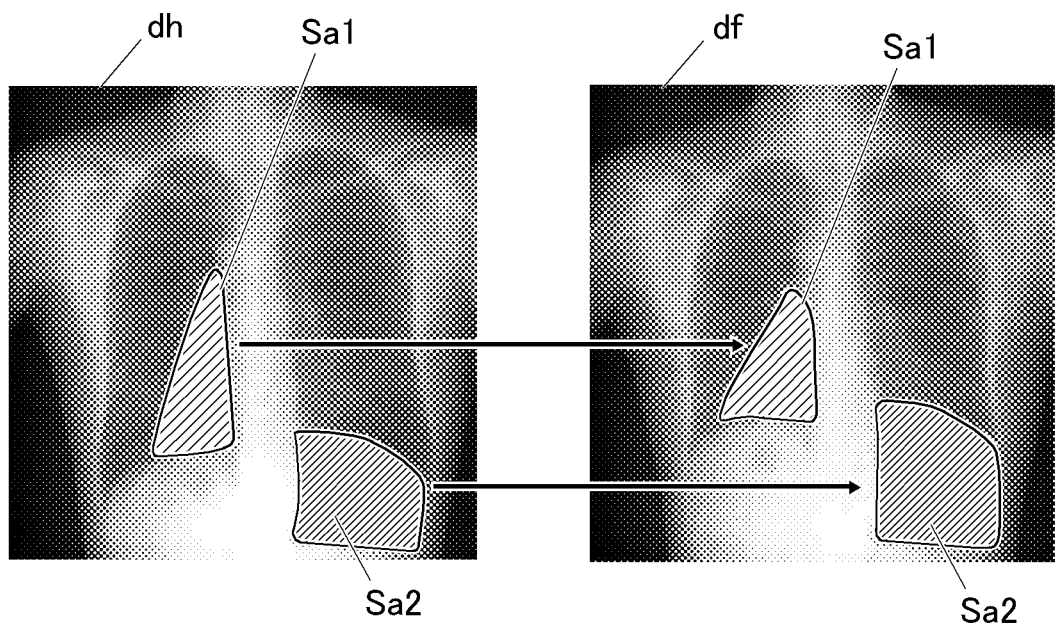
FIG. 4A is an explanation view for explaining position alignment between a reference frame image and the other frame images, showing an example of an image of a chest including a heart and a diaphragm.

For example, in a case of a dynamic image D capturing the site including a chest as shown in FIG. 4A, a structure Sa1 such as a heart which is included in the image performs not only a simple parallel movement but also a movement including deformation such as rotation and expansion/contraction. Thus, them is a high possibility that the accuracy of position alignment is lowered even when the image movement amount of the frame image df after position alignment with respect to the reference frame image dh is small, and thus the position alignment is difficult.

On the other hand, a structure Sa2 such as a diaphragm basically performs a simple movement such as an up-down parallel movement. Thus, the accuracy of position alignment is possibly relatively high even when the image movement amount of the frame image df after position alignment with respect to the reference frame image dh is large.

Thus, in each of the frame images df after position alignment, the accuracy of position alignment is calculated to be low for pixels in the region of structure Sa1 and calculated to be high for pixels in the region of structure Sa2.

Figure 4B:
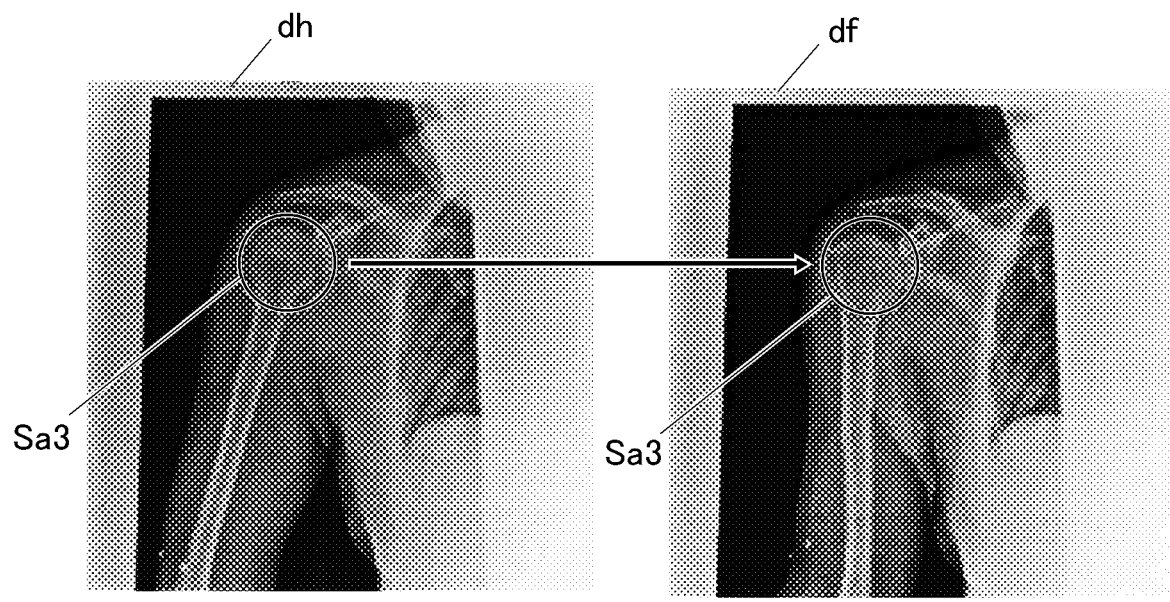
FIG. 4B is an explanation view for explaining position alignment between a reference frame image and the other frame images, showing an example of an image of a portion around a shoulder joint.

In a case of a dynamic image D capturing the movement of twisting an arm for the shape forming site such as a shoulder joint portion as shown in FIG. 4B, a structure Sa3 such as a shoulder joint included in the image (indicated by a circle in FIG. 4B) has a bone that looks largely different between before and after twisting due to a three-dimensional rotation caused by the twisting. Thus, there is a high possibility that the accuracy of position alignment is lowered even when the image movement amount itself of the frame image df after position alignment with respect to the reference frame image dh is small.

Thus, in the frame image df after position alignment, the accuracy of position alignment is calculated to be low for pixels in the region of structure Sa3.

After calculation of the accuracy of position alignment (difference) for each pixel of each of the frame images df after position alignment, the controller 31 as the accuracy calculation unit further calculates the accuracy of position alignment (difference) for the entire frame image df.

FIGS. 5A to 5F show examples of images (difference images) visualizing the accuracies of position alignment (difference) between the reference frame image and the frame images after position alignment in the dynamic image capturing the chest.

In the difference images w (wa to wf) shown in FIGS. 5A to 5F, a pixel having a lower accuracy of position alignment (larger difference) between the reference frame image dh and the frame image df after position alignment is expressed in more white, and a pixel having a higher accuracy of position alignment (smaller difference) is expressed in more black.

The difference image wa shown in FIG. 5A is an example of a frame image df which does not have any pixel portion having a low accuracy of position alignment (large difference) expressed in clear white, and thus has a high accuracy of position alignment.

On the other hand, the difference images wb to wf shown in FIGS. 5B to 5F have portions expressed in a clear white. Especially, the difference image wf shown in FIG. 5F has most pixel portions having low accuracies of position alignment (large differences) expressed in white. Such a difference image wf is an example of a frame image df having a low accuracy of position alignment.

The difference images wb to we shown in FIGS. 5C to 5E especially have low accuracies of position alignment for pixels of the structure Sa1 (for example, heart) shown in FIG. 4A and pixels around the structure Sa1.

After the accuracy of position alignment (difference) for each pixel is calculated for each of the frame images df after position alignment, the controller 31 next calculates a quality value of the composite still image ds generated by combining the reference frame image dh and all the frame images df forming the dynamic image D on the basis of the accuracies of position alignment for each pixel (step S4).

The average value p(i) of accuracies of position alignment for each pixel is calculated and the quality value of the composite still image ds is determined on the basis of the average value p(i), for example.

The average value p(i) of the accuracies of position alignment for each pixel is calculated by the following expressions (1).

In the expression (1), "i" is the number of a pixel forming the frame image df, "N" is the number of frame images df (except for the reference frame image dh) to be combined, and "RegAcc (k, i)" indicates the accuracy of position alignment in the k-th frame image df.

[Formula 1]

$$p(i) = \frac{1}{2}\sum_{k=0}^{N-1} RegAcc(k, i) \quad (1)$$

The quality value of the composite still image ds is determined on the basis of a rate R of the calculated average values p(i) of position alignment accuracies that exceed a predetermined threshold TH. The threshold TH is appropriately set in advance such that a sufficient image quality can be secured when the images are combined with the accuracy of threshold TH or lower.

Since the accuracy of position alignment is lower as the rate R of the p(i) exceeding the predetermined threshold TH is larger, the reciprocal (=1.0−R) is used as the quality value.

For example, the composite still image ds which is composed from frame images df which have relatively high accuracies of position alignment as shown in FIGS. 5A and 5B has a small rate R of p(i) exceeding the predetermined threshold TH. For example, when the rate R of p(i) exceeding the predetermined threshold TH is 10%, the quality value is 90%.

On the other hand, the composite still image ds which is composed from frame images df which have low accuracies of position alignment as shown in FIGS. 5E and 5F has a large rate R of p(i) exceeding the predetermined threshold TH. For example, when the rate R of p(i) exceeding the predetermined threshold TH is 80%, the quality value is 20%.

When the quality value of the composite still image ds is calculated, the controller 31 as the determination unit determines whether or not the composite still image ds can be generated by combining the multiple frame images forming the dynamic image (reference frame image dh and other frame images df after position alignment) (step S5).

To be specific, in the determination of whether or not the composite still image ds can be generated, the controller 31 as the determination unit determines whether or not the quality value of the composite still image ds exceeds a predetermined standard.

The degree of the predetermined standard is appropriately set. For example, the controller 31 determines that the composite still image ds can be generated if the quality value of the composite still image ds exceeds 30%, and the controller 31 determines that the composite still image ds cannot be generated if the quality value is equal to or less than 30%.

Figure 6A:
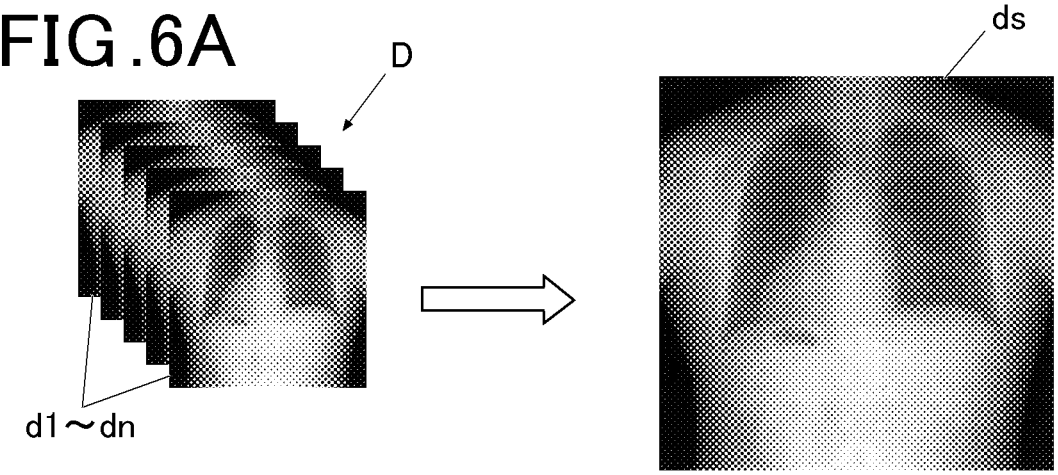
FIG. 6A is a view schematically showing generation of a single composite still image from multiple frame images forming a dynamic image, and shows an example of a case where it is possible to generate a composite still image which has a relatively high quality.
Figure 6B:
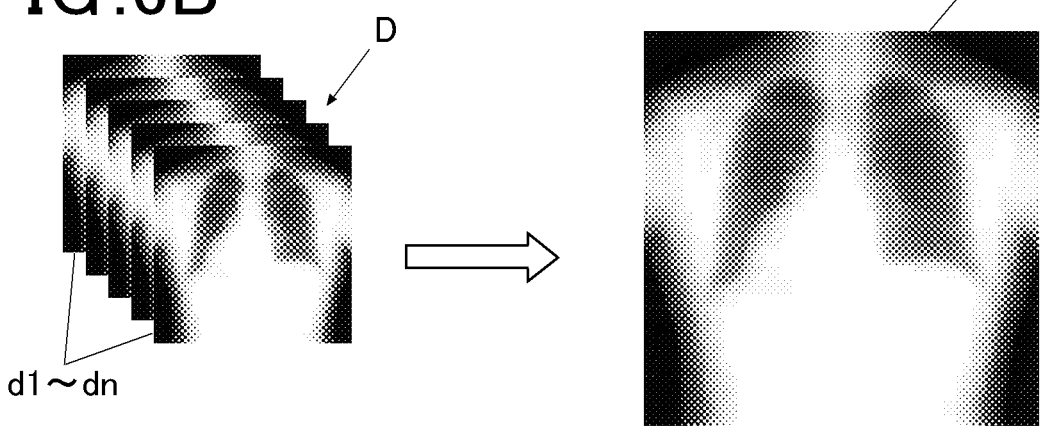
FIG. 6B is a view schematically showing generation of a single composite still image from multiple frame images forming a dynamic image, and shows an example of a case where a composite still image having an intermediate quality between those of FIGS. 6A and 6C is generated.
Figure 6C:
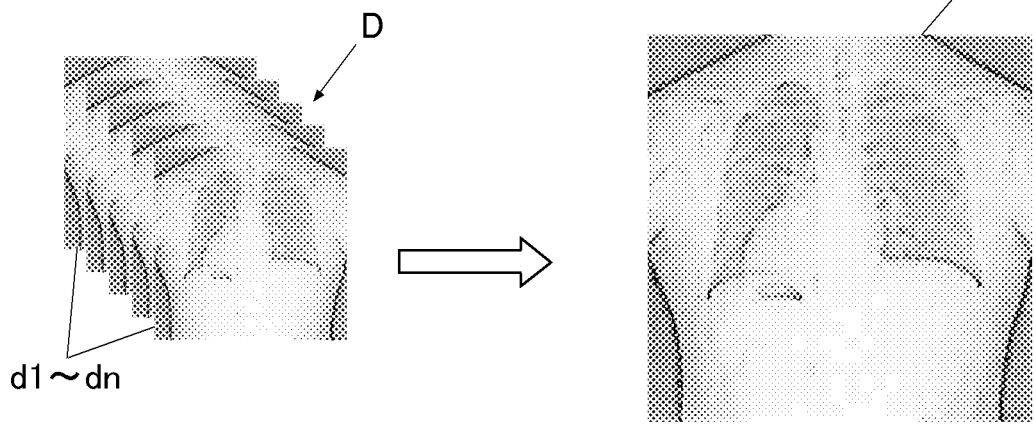
FIG. 6C is a view schematically showing generation of a single composite still image from multiple frame images forming a dynamic image, and shows an example of a case where a composite still image having a low quality is generated.

Each of FIGS. 6A to 6C shows an example of all the frame images df and reference frame image dh forming the dynamic image D on the left side, and an example of the composite still image ds obtained by combining these frame images on the right side.

For example, FIG. 6A schematically shows an example of a composite still image ds obtained by combining frame images df which have relatively high accuracies of position alignment, and the quality value of 90% of the composite still image ds is calculated, for example.

FIG. 6B schematically shows an example of a composite still image ds obtained by combining frame images df which have accuracies of position alignment of 50 to 60%, and the quality value of 40 to 50% of the composite still image ds is calculated, for example.

FIG. 6C schematically shows an example of a composite still image ds obtained by combining frame images df which have low accuracies of position alignment, and the quality value of 20 to 30% of the composite still image ds is calculated, for example.

As mentioned above, in a case where the predetermined standard is set such that the composite still images ds cannot be generated when the quality value of the composite still image ds is equal to or less than 30%, for example, it is determined that the composite still image ds can be generated in the examples shown in FIGS. 6A and 6B, and it is determined that the composite still image ds cannot be generated in the example shown in FIG. 6C.

As the factors causing the quality value of composite still image ds to be equal to or less than tie predetermined standard, for example, there can be considered a case where the image includes a site for which the position alignment is difficult due to complicated or irregular movements for the nature of the structure such as the structure Sa1 shown in FIG. 4A and the structure Sa3 shown in FIG. 4B, and cases where the accuracy of position alignment (registration) excessively gets worse as a whole such as a case where the contrast of anatomical structure is not drawn due to ultralow dose imaging, a case where noise is generated excessively, and a case where the body movement is excessively large.

When the quality value of the composite still image ds is equal to or less than the predetermined standard in such a way, even if the composite still image ds is created in this state, there are possibilities that the image excessively blurs and leads to the deterioration of image quality and cannot be used for diagnosis, or the composite still image ds causing erroneous diagnosis is generated. Thus, even when the composite still image ds is created forcibly, the image cannot be used in diagnosis, and the image creation is a wasted process.

Thus, in the present embodiment, if the controller 31 as the determination unit determines that the composite still image ds cannot be created (step S5; NO), the controller 31 as the display control unit controls the display 34 as a notifier to perform displaying to notify the user that the composite still image ds cannot be created (step S6), and ends the processing.

The notifier is not limited to the display 34. For example, the notification may be performed by an indicator, blinking of a lamp, or the like (not shown in the drawings), or the notification may be made by voice, alarm or the like in a case where a speaker is provided.

On the other hand, if it is determined that the composite still image ds can be created (step S5; YES), the controller 31 as the image combination unit performs weighting of changing the composition ratios for each pixel between the other (that is, other than the reference frame image dh) frame images df after position alignment on the basis of the accuracies of position alignment (step S7). That is, the controller 31 calculates the composition weight (weight coefficient to each pixel of each frame image) according to the accuracy of position alignment calculated by the controller 31 as the accuracy calculation unit.

According to the calculated composition weight, the controller 31 as the image combination unit combines all the frame images d1 to dn (that is, reference frame image dh and the other frames images df after position alignment), and generates a single composite still image ds of a high image quality (composite still image ds shown in the right end of FIG. 3) (step S8).

The composition weight is used for determining the rate of signal value for each pixel of each frame image to be adopted to combine the frame images when the composite still image ds is created. By setting the composition weight to the signal value of each pixel of frame image df after position alignment, the signal value of a pixel having a higher accuracy of position alignment is adopted and reflected at a larger rate in the composite still image ds.

For example, the signal value of a pixel having the composition weight of 0.1 is not adopted much, and the signal value of a pixel having the composition weight of 0.8 or the like is greatly adopted when the images are combined. Thereby, the entire composite still image ds can be made by greatly adopting signal values of pixels having high accuracies of position alignment, and it is possible to make the image having a high image quality and a high resolution.

To be specific, the composite still image ds is generated by the following expression (2).

In the expression (2), "i" indicates the number of a pixel, "N" indicates the number of frame images df to be combined (all the frame images df except for reference frame image dh), "g(i)" indicates the composite still image ds after composition. "h(i)" is the reference frame image dh. "w(k, i)" is the composition weight, "f(k,i)" is the k-th frame image df after position alignment, and "RegAcc (k,i)" indicates the accuracy of position alignment in the k-th frame image df. In the example shown in the embodiment, the accuracy is worse as "RegAcc (k,i)" is larger.

[Formula 2]

$$g(i) = \frac{1}{N+1} h(i) + \frac{N}{N+1} \sum_{k=0}^{N-1} w(k, i) \cdot f(k, i) \quad (2)$$

In the expression (2), "w (k, i)" indicating the composition weight can be represented by the following expression (3).

[Formula 3]

$$w(k, i) = 1.0 - \frac{RegAcc(k, i)}{\sum_{m=0}^{N-1} RegAcc(m, i)} \quad (3)$$

When the composite still image ds is generated, the controller 31 as the display control unit controls the display 34 to display the composite still image ds.

In the present embodiment, the controller 31 causes the display 34 to display the quality value (for example, quality value 90%, quality value 60%, and the like) which is the numerical value indicating the quality of the composite still image ds together with the composite still image ds (step S9).

Thus, by obtaining the dynamic image D, it is possible to obtain the composite still image ds useful for diagnosis and to cause the display 34 to display the composite still image ds, without performing general imaging for obtaining a still image separately from the dynamic imaging.

Furthermore, by displaying the quality value of the composite still image ds together with the composite still image ds, it is possible to provide information regarding reliability of the composite still image ds to the user such as a doctor.

As described above, the program in the present embodiment causes a computer (in the present embodiment, computer configured by including the controller 31 of the diagnostic console 3 and the like) to perform: position aligning that is performing position alignment of other frame images db with respect to one reference frame image dh, the reference frame image dh being selected from among multiple frame images d1 to du forming a dynamic image D, and the other frame images db being other than the reference frame image dh among the multiple frame images d1 to dn; accuracy calculating that is calculating an accuracy of the position alignment for each pixel of each of the other frame images df which are other than the reference frame image dh; and image combining that is combining the reference frame image dh with the other frame images df after the position alignment to generate one composite still image ds. In the image combining, the computer performs weighting and generates the composite still image ds, the weighting being processing of changing composition ratios between the other frame images df for each pixel according to the accuracy calculated by the accuracy calculating.

Thus, it is possible to obtain a still image by merely obtaining the dynamic image D, and it is possible to perform diagnosis by both of an image having motions and a still image.

Since the dynamic image D is obtained by emitting radiation of a relatively low dose, many noises occur in each of the frame images d1 to dn in many cases. The dynamic image D is formed of multiple frame images d1 to dn. If each of the frame images is made to have a resolution equal to the resolution of the still image, the data amount as a whole is excessively heavy, and the load during processing is excessively large. Thus, the resolution is set to be low in many cases. As for this respect, the composite still image dis is generated by combining the multiple frame images d1 to dn. Thereby, it is possible to improve the resolution, remove noise, improve granularity, and the like. Depending on circumstances, it is possible to obtain a composite still image ds of a higher image quality and a higher resolution than the image quality and the resolution of the image originally obtained as a still image.

By generating the composite still image ds from the dynamic image D in such a way, it is not necessary to separately perform imaging for obtaining the still image, and thus it is possible to suppress the exposure dose of the patient to the minimum.

Whether or not an image of a high image quality and a high resolution can be obtained by combining multiple images largely depends on the accuracy of position alignment. For example, as for the heart that repeats dilatation and contraction at the current position and the joint portion that performs three-dimensional rotation movement, for example, the accuracy of position alignment is easily lowered due to the change of shape though the movement amount of the structure is small. On the other hand, as for the structure such as a diaphragm that basically moves by up-down parallel movement, the accuracy of position alignment is possibly high even when the image movement amount is large.

In the present embodiment, such importance of accuracy of position alignment is focused, and weighting (composition weight) at the time of combining the multiple images is determined. Thus, it is possible to generate the composite still image ds of a high image quality and a high resolution.

Thus, it is possible to obtain an excellent composite still image ds which is useful for diagnosis from the multiple frame images d1 to dn forming the dynamic image D.

In the present embodiment, the program further causes the computer to perform displaying that is controlling the display 34 to display the composite still image ds.

Thus, the user such as a doctor can confirm the composite still image ds on the display, which is useful for diagnosis.

In the present embodiment, in the displaying, the computer performs control to display the composite still image ds and controls the display 34 to display a numerical value that indicates a quality of the composite still image ds.

Thus, it is possible to numerically and objectively know how much the image quality or the like of the composite still image ds is reliable, and thus it is possible to perform correct diagnosis.

In the present embodiment, the program further causes the computer to perform: determining that is determining whether or not the composite still image ds is able to be generated from the multiple frame images d1 to dn based on the accuracy calculated by the accuracy calculating, and notifying that is notifying a user that the composite still image ds is not able to be generated in response to determination by the determining that the composite still image ds is not able to be generated.

Thus, it is possible to know that the composite still image ds cannot be generated by notification (for example, displaying of error message) by a notifier (in the present embodiment, display 34). It is possible to prevent unnecessary processing from proceeding, and perform appropriate response such as imaging of a still image.

In the present embodiment, in the determining, the computer determines that the composite still image ds is not able to be generated in response to determination that a quality of the composite still image ds obtained by combining the multiple frame images d1 to dn is to be equal to or less than a predetermined standard.

Thus, it is possible to prevent generation of a composite still image ds of such a quality that is equal to or less than a predetermined standard and cannot be provided for diagnosis, and it is possible to perform appropriate response such as imaging of a still image.

According to the present embodiment, it is possible to obtain a still image of a high image quality by combining multiple frame images forming the dynamic image.

Though the embodiment of the present invention has been described above, the present invention is not limited to the embodiment, and various modifications can be made within the scope of the present invention.

For example, the present embodiment takes, as an example, a case where the diagnostic console 3 in the medical image system 100 functions as the image processing apparatus. However, the image processing apparatus is not limited to this. For example, an independent work station may be provided outside the medical image system 100 such that the dynamic image D is obtained from the medical image system 100 via various types of networks or the like.

The present invention is not limited to a case of having a single predetermined threshold TH and a single threshold at the time of determining whether or not the quality of composite still image ds is equal to or less than a predetermined standard, for example.

For example, there may be multiple predetermined thresholds TH and multiple thresholds at the time of determining whether or not the quality of composite still image ds is equal to or less than a predetermined standard so that different thresholds are used in different cases such as in a case of requiring more strict high standard and a case of intending to generate a still image even if the standard is a little low, according to the usage of composite still image ds and the characteristic of the site which is the imaging target.

When different thresholds are used for different cases, the user may set a desired threshold arbitrarily, or the controller 31 may automatically set an appropriate threshold according to the type of an imaging site or the like.

As for the other detailed configurations and detailed operations of the components forming the image processing apparatus (diagnostic console 3 in the present embodiment), modifications can be appropriately made within the scope of the present invention.

Although embodiments of the present invention have been described and illustrated in detail, the disclosed embodiments are made for purposes of illustration and example only and not limitation. The scope of the present invention should be interpreted by terms of the appended claims.

What is claimed is:

1. A non-transitory recording medium storing a computer readable program that causes a computer to perform:
    performing position alignment of other frame images with respect to one reference frame image, the one reference frame image being a reference frame image selected from among multiple frame images that form a dynamic image, and the other frame images being other than the reference frame image;
    calculating an accuracy of the position alignment for each pixel of each of the other frame images;
    determining whether or not one composite still image is able to be generated from the multiple frame images based on the calculated accuracy;
    combining the reference frame image with the other frame images after the position alignment to generate the one composite still image; and
    calculating a quality value of the composite still image based on an average value of the accuracies of position alignment for the each pixel, wherein
    in the combining, the computer performs weighting and generates the one composite still image, the weighting being processing of changing a composition ratio between the other frame images for each pixel according to the calculated accuracy.

2. The recording medium according to claim 1, wherein the program further causes the computer to perform displaying the one composite still image.

3. The recording medium according to claim 2, wherein, in the displaying, the computer performs control to display the one composite still image and performs control to display a numerical value that indicates a quality of the one composite still image.

4. The recording medium according to claim 1, wherein the program further causes the computer to perform:
    notifying a user that the one composite still image is not able to be generated in response to determination by the determining that the one composite still image is not able to be generated.

5. The recording medium according to claim 1, wherein, in the determining, the computer determines that the one composite still image is not able to be generated in response to determination that a quality of the one composite still image obtained by combining the multiple frame images is to be equal to or less than a predetermined standard.

6. An image processing apparatus comprising a hardware processor that:
    performs position alignment of other frame images with respect to one reference frame image, the one reference frame image being a reference frame image selected from among multiple frame images that form a dynamic image, and the other frame images being other than the reference frame image;
    calculates an accuracy of the position alignment for each pixel of each of the other frame images;
    determines whether or not one composite still image is able to be generated from the multiple frame images based on the calculated accuracy; and
    combines the reference frame image with the other frame images after the position alignment to generate one composite still image; and
    calculates a quality value of the composite still image based on an average value of the accuracies of position alignment for the each pixel, wherein
    the hardware processor performs weighting and generates the one composite still image, the weighting being processing of changing a composition ratio between the other frame images for each pixel according to the calculated accuracy.

7. An image processing method comprising:
    performing position alignment of other frame images with respect to one reference frame image, the one reference frame image being a reference frame image selected from among multiple frame images that form a dynamic image, and the other frame images being other than the reference frame image;
    calculating an accuracy of the position alignment for each pixel of each of the other frame images;
    determining whether or not one composite still image is able to be generated from the multiple frame images based on the calculated accuracy;
    combining the reference frame image with the other frame images after the position alignment to generate one composite still image; and
    calculating a quality value of the composite still image based on an average value of the accuracies of position alignment for the each pixel, wherein
    in the step of combining, weighting is performed and the one composite still image is generated, the weighting being processing of changing a composition ratio between the other frame images for each pixel according to the calculated accuracy.

* * * * *